(12) United States Patent
Slugovc et al.

(10) Patent No.: US 8,981,024 B2
(45) Date of Patent: Mar. 17, 2015

(54) OLEFIN METATHESIS

(75) Inventors: Christian Slugovc, Graz (AT); Julia Wappel, Pinggau (AT)

(73) Assignee: Technische Universität Graz, Graz (AT)

( * ) Notice: Subject to any disclaimer, the term of this patent is extended or adjusted under 35 U.S.C. 154(b) by 0 days.

(21) Appl. No.: 14/241,897

(22) PCT Filed: Sep. 3, 2012

(86) PCT No.: PCT/AT2012/050124
§ 371 (c)(1),
(2), (4) Date: Mar. 14, 2014

(87) PCT Pub. No.: WO2013/029079
PCT Pub. Date: Mar. 7, 2013

(65) Prior Publication Data
US 2014/0213746 A1    Jul. 31, 2014

(30) Foreign Application Priority Data
Sep. 2, 2011 (AT) ................................ A 1258/2011

(51) Int. Cl.
*C07F 11/00* (2006.01)
*C07F 15/00* (2006.01)
*B01J 31/34* (2006.01)
*B01J 31/28* (2006.01)
*B01J 31/18* (2006.01)
*C07D 215/30* (2006.01)
*C07C 2/52* (2006.01)
*C08F 132/08* (2006.01)
*C08G 61/08* (2006.01)

(52) U.S. Cl.
CPC .............. *B01J 31/182* (2013.01); *C07D 215/30* (2013.01); *C07F 15/0046* (2013.01); *C07C 2/52* (2013.01); *C08F 132/08* (2013.01); *C08G 61/08* (2013.01); *C08G 2261/418* (2013.01); *C08G 2261/419* (2013.01); *B01J 2231/48* (2013.01); *B01J 2531/821* (2013.01)
USPC ............... 526/171; 556/57; 556/58; 556/136; 556/137

(58) Field of Classification Search
CPC ........ B01J 31/34; B01J 31/28; B01J 2531/64; B01J 2531/66; B01J 2531/821; B01J 31/1825; C07F 11/00; C07F 15/00
USPC ...................... 556/57, 58, 136, 137; 526/171
IPC .............................. C08F 15/0046, 15/00, 11/00
See application file for complete search history.

(56) References Cited

PUBLICATIONS van der Schaaf et al. Organometallics, 1994, 13, 1433-1444.*
Guari et al. Organometallics, 1996, 15, 3471-3473.*
Denk et al. Adv. Synth. Catal., 2002, 334, 666-670.*
Office Action for A 1258/2011-1 (Austria Patent Office) dated Jul. 6, 2012.
Written Opinion for PCT/AT2012/050124 (EPO) dated Nov. 15, 2012.
Allaert, Bart et al., "Synthesis and activity for ROMP of bidentate Schiff base substitute second generation Grubbs catalysts," Journal of Molecular Catalysis A: Chemical (Aug. 24, 2006) 221-226.
Burtscher, Daniel et al., "Controlled Living Ring-Opening Metathesis Polymerization with a Ruthenium Indenylidene Initiator," J. Polym. Sci. Part A: Polym. Chem. (2008) Vol. 46 pp. 4630-4635.
Denk, Karin et al., "N-Heterocyclic Carbenes, Part 33: Combining Stable NHC and Chelating Pyridinyl-Alcoholato Ligands: A Ruthenium Catalyst for Applications at Elevated Temperatures," Adv. Synth. Catal. (2002) 334 No. 6+7 pp. 666-670.
Garber, Steven B. et al., "Efficient and Recyclable Monomeric and Dendritic Ru-Based Metathesis Catalysts," J. Am. Chem. Soc. (Apr. 4, 2000) vol. 122 pp. 8168-8179.
Hahn, F. Ekkehardt, et al., "Systhesis, characterization, and catalytic activity of a ruthenium carbene complex coordinated with bidentate 2-pyridine-carboxylato ligands," Journal of Organometallic Chemistry (Aug. 30, 2005) vol. 690 pp. 5816-5821.
Samec, Joseph S.M., et al., "Latent ruthenium olefin metathesis catalysts featuring a phosphine or an N-heterocyclic carbene ligand," Journal of Organometallic Chemistry (Apr. 24, 2010) vol. 695 pp. 1831-1837.
Trnka, Tina M., et al., "The Development of L2x2Ru==CHR Olefin Metathesis Catalysts: An Organometallic Success Story," Acc. Chem. Res. (2001) Vol. 34, No. 1, pp. 18-29.

* cited by examiner

*Primary Examiner* — Rip A Lee
(74) *Attorney, Agent, or Firm* — Chainey P. Singleton; Edwin S. Flores; Chalker Flores, LLP

(57) ABSTRACT

The present invention relates to pre-catalysts for olefin metathesis and composition involving these pre-catalysts.

28 Claims, 5 Drawing Sheets

OLEFIN METATHESIS

The present invention relates to pre-catalysts for olefin metathesis.

Olefin metathesis is a fundamental catalytic reaction, which is one of the view and particularly economically interesting methods, to form carbon-carbon-bonds and also complex molecules, particularly in the field of pharmacy.

During the course of the reaction carbon-carbon-double bonds are cleaved and formed under simultaneous exchange of substituents, via ring closing, ring opening or polymerization. In In the following the term "olefin metathesis" or short "metathesis" is used also for mechanistically related reactions such as alkyne metathesis, enyne metathesis etc.

Especially petrochemical-, polymer- and specialized chemistry have developed metathesis over approximately half a century to form simple carbon compounds.

Since the discovery of the metathesis reaction mechanism by Grubbs, Schrock and Chauvin, many important inventions, such as the 1$^{st}$, 2$^{nd}$ and 3$^{rd}$ Grubbs catalysts or the so called "Hoveyda-Grubbs" catalyst (the first chelating pre-catalyst) have been made and used in the different forms of metathesis.

Especially the Ring Opening Metathesis Polymerization (ROMP) for the preparation of special functionalized polymeric materials and the Ring Closing Metathesis (RCM) for instance for pharmaceutical products has gained more and more interest.

For many applications, especially for industrial uses such as RIM processes (reaction injection moulding), the processability of the starting substrate and the pre-catalyst is desired. It is beneficial when the pre-catalyst and the monomer can be mixed and stored together, without any reaction taking place. This can be realized when thermally, photochemically or chemically triggered pre-catalysts with latent characteristics are used. The ideal latent catalyst is totally inactive prior to activation and can be triggered quantitatively to a highly active form. Many of these latent catalysts possess a chelating moiety.

One possible way for such triggerable pre-catalysts, is the introduction of a chelating anionic moiety, whereas one or two chlorides can be substituted. So far, catalysts featuring Schiff base-, picolinate-, pyridinyl, alcoholate- and proline ligands forming a five or six membered ring have been reported. (B. Allaert, et al. A: Chem. 260(2006):221-226; J. S. M. Samec, et al. J. Organomet. Chem. 695(2010):1831-1837; E. G. Hahn, et al. J. Organomet. Chem. 690(2005):2816-5821; K. Denk, et al. Adv. Synth. Catal. 344(2002):666-670). WO2007/022945 A2 for example describes the preparation of tetra- or penta-coordinated Schiff base catalysts and their use.

Important for all these systems and the application in industrial scale, is a simple, straight forward and economically friendly synthesis with high yields.

An object of the present invention is the provision of metathesis pre-catalysts which overcome the disadvantages of the techniques currently used in the art.

The present invention relates to a compound with the general formula (I):

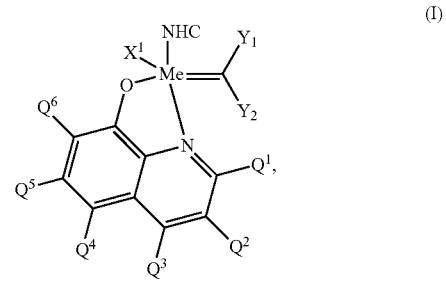

wherein
$X^1$ is selected from the group consisting of halogens, preferably Cl, Br or I, pseudohalogens, trifluoroacetic acid, carboxylates and a $\kappa^2$ (N,O) bound 8-quinolinlate of the general formula (II)

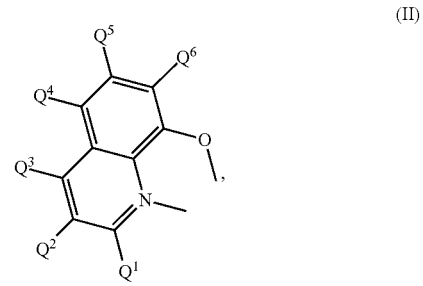

$Q^1$, $Q^2$, $Q^3$, $Q^4$, $Q^5$ and $Q^6$ equal or unequal selected onefoldly or manifoldly independently from each other from the group consisting of hydrogen, halogens, cyano, $C_1$ to $C_6$-alkyl (preferably $C_1$ to $C_3$-alkyl), aryl, benzyl, nitro, hydroxyl, sulfonic acid, arylsulfonyl, —OR$^a$, —NR$^a{}_2$, —CX$^b{}_3$, and —COR$^a$, wherein R$^a$ is H or $C_1$ to $C_6$-alkyl (preferably $C_1$ to $C_3$-alkyl) and X$^b$ is F, Cl or Br, $Y^1$ and $Y^2$ are independently selected from the group consisting of hydrogen $C_1$ to $C_6$-alkyl, aryl,

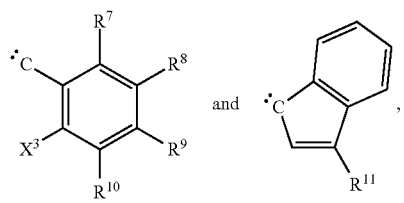

wherein
$X^3$ is selected from the group consisting of hydrogen, —OR$^6$, —COH, —COR$^6$, —COOR$^6$—SR$^6$, SOR$^6$, SO$_2$R$^6$, whereas R$^6$ can be a functionalized, branched or unbranched $C_1$ to $C_6$-alkyl group (preferably $C_1$ to $C_3$-alkyl),
$R^7$, $R^8$, $R^9$ and $R^{10}$ are independently from each other selected from the group consisting of hydrogen, $C_1$ to $C_6$ alkyl (preferably $C_1$ to $C_3$-alkyl), halogens, nitro and $C_1$ to $C_6$-alkoxy, particularly —OCH$_3$, whereas two adjacent substituents can form an additional aromatic ring with each other (e.g. substituted or unsubstituted indenylidene rings), $R^{11}$ is a substituted or unsubstituted aryl group,
NHC is a N-heterocyclic carbene and
Me is a metal selected out of the group of ruthenium, molybdenum and tungsten.

The present invention relates also to a compound with the general formula (I):

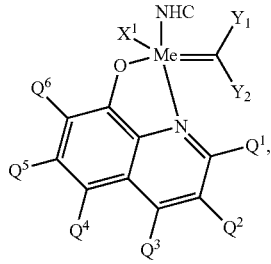
(I)

wherein $X^1$ a $\kappa^2$ (N,O) bound 8-quinolinlate of the general formula (II)

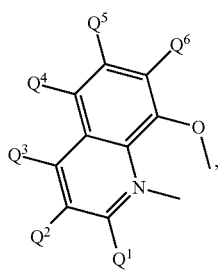
(II)

$Q^1$, $Q^2$, $Q^3$, $Q^4$, $Q^5$ and $Q^6$ equal or unequal onefoldly or manifoldly independently selected from the group consisting of hydrogen, halogens, cyano, $C_1$ to $C_6$-alkyl (preferably $C_1$ to $C_3$-alkyl), aryl, benzyl, nitro,hydroxyl, sulfonic acid, arylsulfonyl, —$OR^a$, —$NR^a_2$, —$CX^b_3$, and —$COR^a$, whereas $R^a$ H or $C_1$ to $C_6$-alkyl (preferably $C_1$ to $C_3$-alkyl) and $X^b$ is F, Cl or Br, $Y^1$ and $Y^2$ are independently selected from the group consisting of hydrogen $C_1$ to $C_6$-alkyl, aryl,

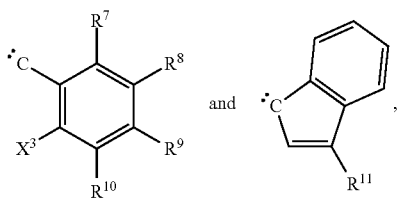

wherein
$X^3$ is selected from the group consisting of hydrogen, —$OR^6$, —COH, —$COR^6$, —$COOR^6$—$SR^6$, $SOR^6$, $SO_2R^6$, wherein $R^6$ is optionally a functionalized, branched or unbranched $C_1$ to $C_6$-alkyl group (preferably $C_1$ to $C_3$-alkyl), $R^7$, $R^8$, $R^9$.$R^{10}$ is independently selected from the group consisting of hydrogen, $C_1$ to $C_6$ alkyl (preferably $C_1$ to $C_3$-alkyl), halogens, nitro and $C_1$ to $C_6$-alkoxy, particularly —$OCH_3$, wherein two adjacent substituents can form an additional aromatic ring with each other, $R^{11}$ is a substituted or unsubstituted aryl group,
NHC is an N-heterocyclic carbene and
Me is a metal selected from the group consisting of ruthenium, molybdenum and tungsten, wherein this compound has the following general formula:

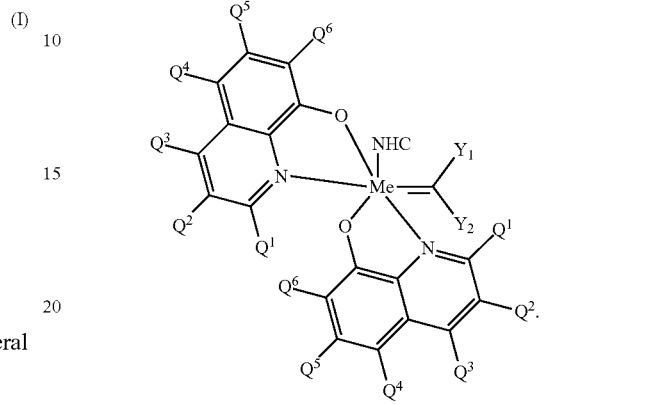
(VII)

Especially preferred are compounds with the formula (I) and (VII), where the metal (Me) is ruthenium.

The present invention relates to new metathesis pre-catalysts, which are able to trigger or initiate the metathesis reaction through the addition of acid to the corresponding reaction mixture. The inventive pre-catalysts comprise a 8-quinolinlate, which is directly bound via a $\kappa^2$ (N,O)-bond to the ruthenium center.

The catalysts according to the invention are solely triggered via the addition of acid and exhibit an outstanding solubility in a variety of compounds, especially in apolar solvents and monomers, especially in dicyclopentadiene (DCPD).

A major advantage of the compounds of the present invention is its outstanding solubility in DCPD and other apolar substances. Furthermore all those compounds possess a good thermal and oxidative stability. The switchability with acid ensures a simple handling. Additionally, the inventive compounds are synthesized easily, quickly and cheap.

The term "$C_1$-$C_6$-alkyl" refers to acyclic straight (e.g. ethyl) or acyclic branched (e.g. isopropyl) alkyl substituents containing from one to six carbon atoms. The term can also be used in combination with other substituent (e.g. fluoroalkyl).

The term "aryl" refers to aromatic systems which can be either monocyclic (e.g. phenyl) or bicyclic (e.g. naphtyl). The term can also be used in combination with other substituents (e.g. arylthio).

The term "$C_1$-$C_6$ alkoxy" refers to a functional group based on the general formula —O—$C_xH_y$ (e.g. $OCH_3$), containing from one to six carbon atoms.

The N-heterocylcic carbene (NHC) is preferably a saturated or unsaturated carbene of the general formula (III) or (IV)

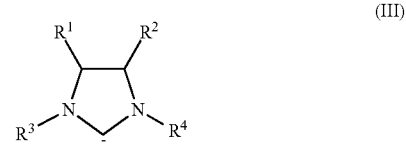
(III)

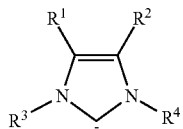

(IV)

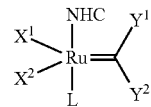

(VI)

wherein $R^1$ and $R^2$ are each independently selected from the group consisting of hydrogen, $C_1$-$C_6$ alkyl and aryl, or a ring with 5 to 7 carbon atoms and $R^3$ and $R^4$ are each independently selected from the groups of alkyl, aryl and phenyl wherein the phenyl residue is optionally substituted three times with hydrogen, branched or unbranched $C_1$-$C_6$ alkyl residues and/or halogen residues.

According to a preferred embodiment of the present invention, the N-heterocyclic carbene (NHC) is selected from the group consisting of H₂IMes (1,3-Dimesityl-Imidazolidin-2-yliden), IMes (1,3-Dimesityl-Imidazol-2-yliden), SIPr (1,3-bis(2,6-Diisopropylphenyl)-4,5-Dihydroimidazol-2-yliden) and IPr (1,3-bis(2,6-Diisopropylphenyl)-4,5-Imidazol-2-yliden).

$Y^1$ is preferably selected from the group consisting of phenyl and phenyl-indenylidene and $Y^2$ is preferably hydrogen.

According to a preferred embodiment of the present invention, the 8-quinolinlate is selected from the group consisting of non-substituted 8-quinolinlate, 5,7-dichloro-8-quinolinolate and 5,7-dibromo-8-quinolinlate.

Especially preferred are compounds with the general formula (I) and (VII) as depicted in the examples.

According to a preferred embodiment of the present invention the compound of the present invention is selected from the group consisting of (H₂IMes)Cl(5,7-dichloro-8-quinolinolate)Ru(3-phenyl-indenylidene), (H₂IMes)(5,7-dichloro-8-quinolinolate)₂Ru(3-phenyl-indenylidene), (H₂IMes)(5,7-dichloro-8-quinolinolate)₂Ru(CH-o-OiPrC₆H₄), (H₂IMes)Cl(5,7-dibromo-8-quinolinolate)Ru(3-phenyl-indenylidene), (H₂IMes)(5,7-dibromo-8-quinolinolate)₂Ru(3-phenyl-indenylidene) and (H₂IPr)(5,7-dichloro-8-quinolinolate)₂Ru(3-phenyl-indenylidene).

A further aspect of the present invention relates to a method for the preparation of a compound according to the present invention.

The method according to the present invention comprises the step of reacting a 8-quinolinolate with the general formula (V)

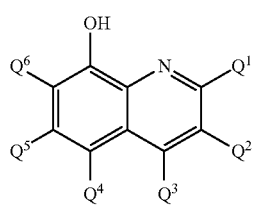

(V)

with an alkylidene of the general formula (VI)

in the presence of a base, e.g. cesium carbonate, potassium carbonate and thallium carbonate and an organic solvent.

The 8-quinolinlate substituted complexes based on ruthenium, molybdenum or tungsten are synthesized by the reaction of a corresponding alkylidene precursor with the general formula VI in the presence of a base (e.g. cesium carbonate) with the corresponding 8-hydroxyquinoline derivative to obtain the newly invented pre-catalyst in high yields. Especially good results are obtained using cesium carbonate as the base.

The compound of the present invention can be synthesized in various ways using a variety of different starting materials. Preferred starting compounds for the anionic ligand exchange of the invention are (Py)(H₂IMes)(Cl₂)Ru(3-phenyl-1H-inden-1-ylidene) (D. Burtscher, et al. *J. of Polym. Science: Polymer Chemistry* 46(2008):4630-4635) representing a phosphine free Ru compound with a sterically demanding indenylidene carbene, (PPh₂)(H₂IMes)(Cl₂)Ru(3-phenyl-1H-inden-1-ylidene) representing a phosphine containing starting material and (H₂IMes)Cl₂Ru(CH-o-OiPrC₆H₄) (S. B. Garber, et al. *J. Am. Chem. Soc.* 122(2000):8168-8179) standing for a phosphine free compound with a chelating carbene ligand. All three starting complexes can be obtained in a high yield, which makes them to economical starting materials. Of course it is also possible to use other compounds as starting material.

The use of phosphine scavengers such as Cu(I)Cl is not required during the formation of the new invented catalysts, even if the phosphine containing starting material (PPh₂)(H₂IMes)(Cl₂)Ru(3-phenyl-1H-inden-1-ylidene) is used. That results in high purity materials with simple workup procedures.

The general preparation manner is, to dissolve the alkylidene starting material in an appropriate solvent, most preferably CH₂Cl₂, and to add the corresponding base, most preferably Cs₂CO₂, and the 8-hydroxyquinoline derivative. The reaction is preferably carried out at room temperature overnight. Due to the great stability of the starting material and the new pre-catalysts, the use of dry solvents is not required.

The method of the present invention provides yields between 65 and 90%, depending on the 8-hydroxyquinoline derivative, the base and the Ru-precursor used.

Good results can be obtained when the 8-hydroxyquinoline derivative used is not soluble in the utilized solvent. Due to the insolubility of cesium carbonate in organic solvents, this facilitates purification and enables an easy workup just by filtration of the undissolved products. In some cases, different derivatives are formed. The two derivatives can be a mono- and a disubstituted catalyst or two, with two 8-quinolinolate substituted products. The separation of these two products requires the use of a column chromatography. If the two derivatives are used together without separation, workup is very easy (just by filtration) and economically friendly and makes the catalysts well suited for industrial uses.

A further aspect of the present invention relates to a catalyst composition comprising a compound according to the present invention.

A further aspect of the present invention relates to the use of a compound or a composition according to the present invention as pre-catalyst for an olefin metathesis.

The compound of the present invention can be used in various metathesis reactions. Especially the application in ROM polymerizations reactions is a promising field for the catalysts of the present invention. Due to the unexpected observation, that the new catalysts are soluble in almost every apolar solvent or substrate, solvent free reactions can be performed.

Therefore the compound and the composition of the present invention is most preferably used for the ring opening metathesis polymerization of cyclic olefin, metathesis of cyclic olefins, acyclic diene metathesis, cross-metathesis of cyclic and acyclic olefins, ring closing metathesis, metathesis depolymerization of unsaturated polymers or metathesis of functionalized olefins.

Combining these special characteristic of latency and the extraordinary solubility of the catalysts, they are well qualified for, for instance, the solvent free ROM polymerization of very reactive monomers such as dicylcopentadiene.

A further aspect of the present invention relates to a procedure for olefin metathesis, especially for ring opening metathesis polymerization of cyclic olefins, metathesis of cyclic olefins, acyclic diene metathesis, cross-metathesis of cyclic and acyclic olefins, ring closing metathesis, metathesis depolymerization of unsaturated polymers or metathesis of functionalized olefins, in the presence of a compound comprising a contacting step with at least one olefin with a compound, that activates the olefin metathesis via the addition of an acid, whereby the olefin metathesis most preferably is a ring opening metathesis polymerization of dicyclopentadiene.

A further aspect of the present invention relates to a method for olefin metathesis in the presence of a compound or composition according to the present invention comprising a contacting step with at least one olefin with a compound or composition according to the present invention, whereby an acid is added to the emerging mixture to start the olefin metathesis.

Therefore, the acid used is most preferably an inorganic acid selected out of the group consisting of HCl, HBr or other hydrogen halides or a compound selected out of a group which can release HCl via the reaction with water (e.g. $SiCl_4$).

A major advantage of the pre-catalysts of the present invention is their latent character, due to the chelating 8-quinolinolate moieties. Monomer and pre-catalyst can be easily combined with each other to a homogenous reaction solution and afterwards initiated by acid. A preferred acid for the activation of the compounds of the present invention is hydrochloric acid. HCl can be used either as an aqueous- or as an etherical solution.

In contrast to many other latent catalysts, these compounds of the present invention are not activated by the means of heat. Heating of the monomer/pre-catalyst mixture does not result in any metathesis reaction. This again favors the mixing and preparation of the substrate and pre-catalyst without any reaction happening.

According to a preferred embodiment of the present invention the acid is added in a defined ratio of 1 eq to 150 eq, most preferable between 10 eq and 50 eq.

According to a preferred embodiment of the present invention the olefin metathesis is conducted at a temperature between 15° C. and 90° C., most preferable between 20° C. and 80° C.

Although the olefin metathesis is not started via temperature increase when the present invention is used, the temperature increase can possibly accelerate the rate of the conversion.

According to a preferred embodiment of the present invention the olefin metathesis is a ring opening metathesis polymerization of cyclic olefins, a metathesis of cyclic olefins, acyclic diene metathesis, cross-metathesis of cyclic and acyclic olefins, ring closing metathesis, metathesis depolymerization of unsaturated polymers or metathesis of functionalized olefins.

The present invention is shown in the following figures and examples, without being restricted thereto.

EXAMPLES

Figure 1:
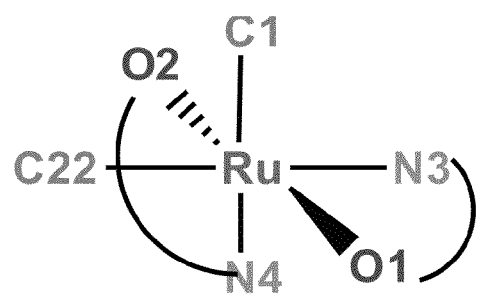
FIG. 1 shows a schematic representation and a ball-and-stick model of derivative 3 from example 2.
Figure 1:
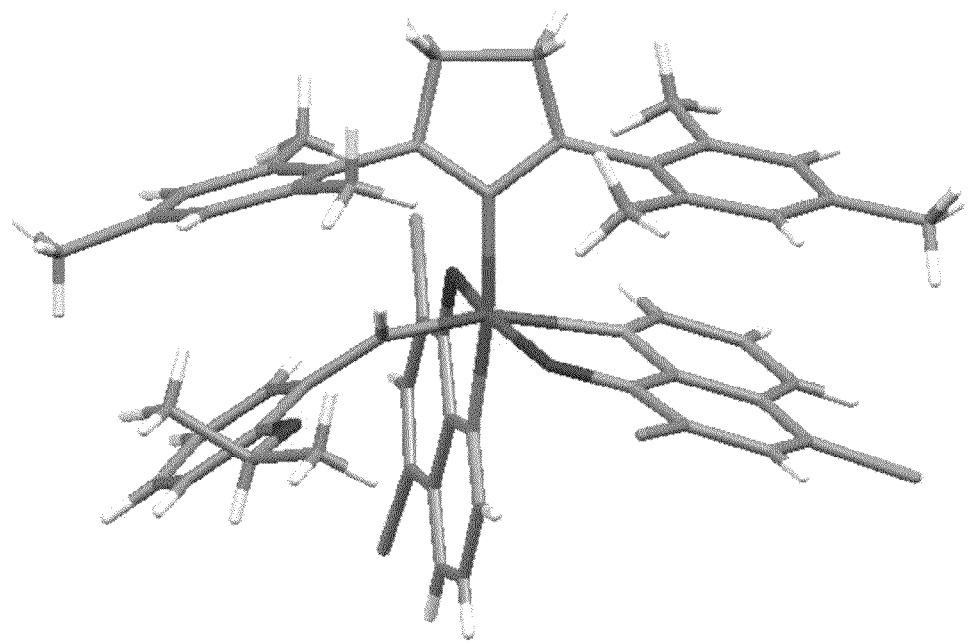
Figure 2:
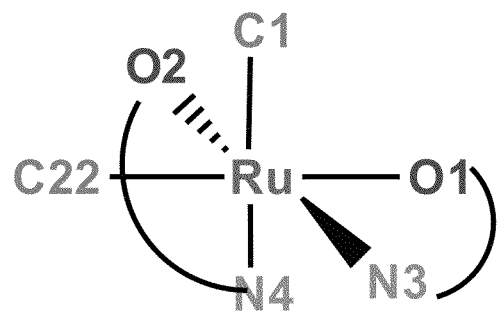
FIG. 2 shows an schematic representation and a ball-and-stick model of derivative 4 from example 2.
Figure 2:
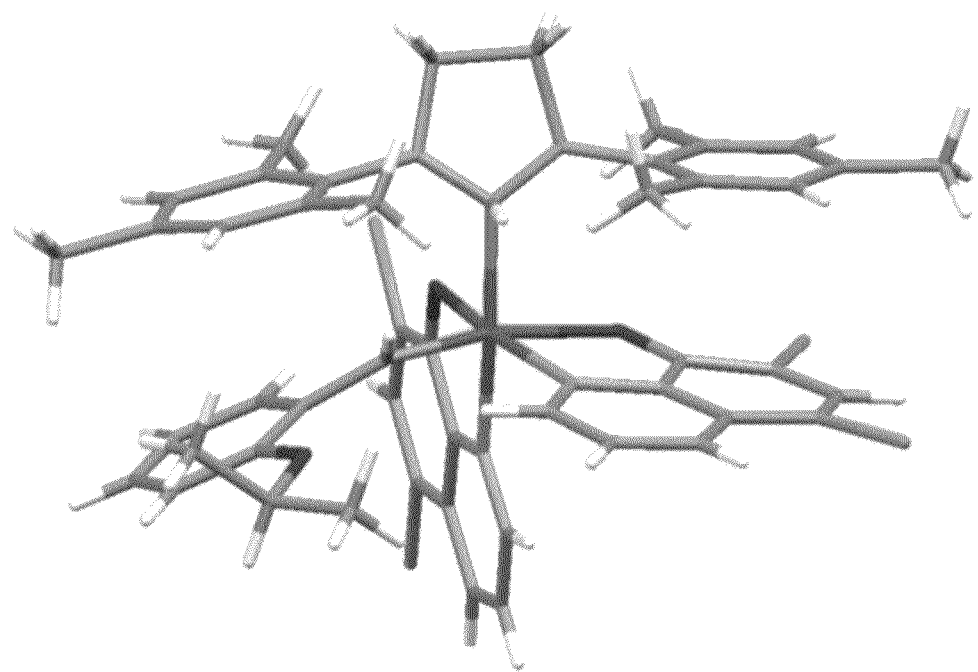

The 8-hydroxyquinolines used in the following examples and the methods for their synthesis, respectively, are well described in the prior art.

Starting material M20 (($PPh_3$)($H_2IMes$)($Cl_2$)Ru(3-phenyl-1H-inden-1-ylidene)) and M31 ((Py)($H_2IMes$)($Cl_2$)Ru(3-phenyl-1H-inden-1-ylidene)) were obtained from Umicore AG & Co KG (Germany).

($H_2IMes$)$Cl_2$Ru(CH-o-$OiPrC_6H_4$) was prepared by adopting Hoveyda's protocol (S. B. Garber, et al. J. Am. Chem. Soc. 122 (2000) :8168-8179. M2 (($PCy_3$)($H_2IMes$)($Cl_2$)Ru (3-phenyl-1H-inden-1-ylidene)) instead of G2 (($PCy_3$)($H_2IMes$)($Cl_2$)Ru(benylidene)) and 1-isopropoxy-2-(prop-1-en-1-yl)benzene was used instead. The reaction yielded the desired product in 78% yield.

DCPD was obtained from Aldrich and consists of around 95% endo and 5% exo isomers (The term DCPD refers to any mixture of endo- and exo-isomers).

Example 1

Preparation of (H₂IMes)Cl(5,7-dichloro-8-quinolinolate)Ru(3-phenyl-indenylidene) and (H₂IMes)(5,7-dichloro-8-quinolinolate)₂Ru(3-phenyl-indenylidene)

Synthesis Way A

Equation 1:

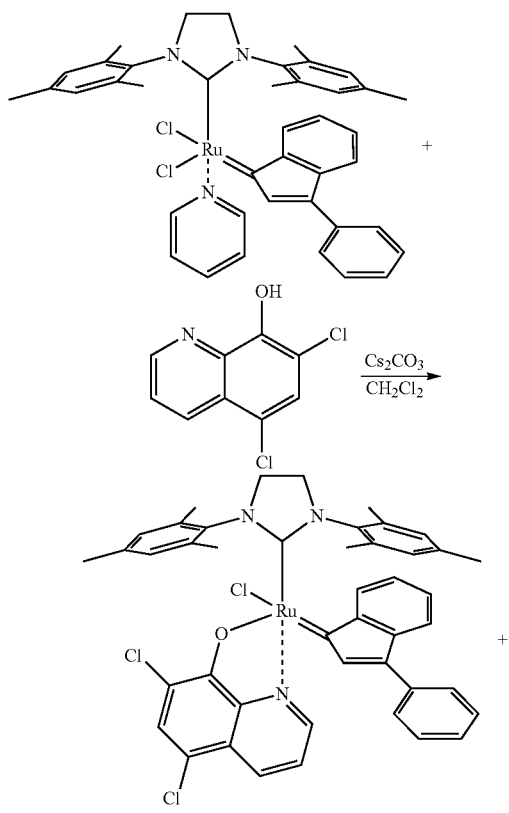

In a Schlenk flask M31 (Py)(H₂IMes)(Cl₂)Ru(3-phenyl-1H-inden-1-ylidene) (142 mg, 0.189 mmol, 1 eq) was dissolved in degassed CH₂Cl₂ (≈18 mL). 5,7-Dichloro-8-hydroxyquinoline (810 mg, 3.785 mmol, 20 eq) and Cs₂CO₃ (1.24 g, 3.815 mmol, 20 eq) were added. The reaction mixture was stirred in a Schlenk flask under argon atmosphere overnight.

The insoluble residue was filtered over celite. According to a TLC (CH/EE 5:1) two derivatives were formed. The two catalysts were separated via column chromatography (CH/EE 10:1) and fully characterized by NMR. Yield=90% (117 mg 1 and 33 mg 2).

1: $^1$H-NMR (δ, 20° C., CDCl₂, 300 MHz): 8.0 (d j=8.1 Hz, 1H, CH$^{hq\ 3}$), 7.97 (d j=4.8 Hz, 1H, CH$^{hq\ 1}$), 7.74 (d j=8.1 Hz, CH), 7.30 (t, 2H, CH), 7.05 (s, 2H, CH), 7.23 (d, 2H, CH), 7.12 (d j=7.14 Hz, 1H, CH), 7.03 (q, 1H, CH$^{hq\ 2}$), 6.44 (s, 3H CH), 6.23 (s, 2H, CH), 6.20 (d, 1H, CH), 3.87 (s, 4H, CH₂), 2, 32, 2.08, 1.92 (s, 18H, CH₃$^{mes\ 7,7',8,8',9,9'}$).

$^{13}$C-NMR (δ, 20° C., CDCl₃, 300 MHz): Ru=C and Ru—C not observed, 167.2 (C$_q$), 164.6 (CH), 146.7 (CH), 143.8 (C$_q$), 143.2 (CH), 142.8 (CH), 141.8 (C$_q$), 129.1 (CH), 128.7 (CH), 128.0 (CH), 127.9 (CH), 127.6 (CH), 126.0 (C$_q$), 125.9 (CH), 125.7 (C$_q$), 121.8 (CH), 121.0 (CH), 118.9 (C$_q$), 118.5 (C$_q$), 117.6 (CH), 111.7 (C$_q$), 109.3 (C$_q$), 51.6 (2C, CH₂—N), 20.9, 18.1 (12C, CH₃).

2: $^1$H-NMR (δ, 20° C., CDCl₃, 300 MHz): 8.15 (d j=4.8 hZ, 1H, CH$^{hq\ 1}$), 7.99 (dd j=8.4, 1H, CH$^{hq\ 3}$), 7.9 (3H, CH$^{hq\ 3}$), 7.60 (1H, CH), 7.52 (1H, CH), 7.47 (1H, CH), 7.31 (s, 1H, CH), 7.24 (s, 1H, CH), 7.2 (t, 2H, C$^{ind\ 2\ or\ 3}$), 6.81 (q, 1H, CH$^{hq\ 2}$), 6.65 (t, 1H, CH$^{ind\ 2\ or\ 3}$), 6.53 (s, 2H, CH$^{mes}$), 6.50 (q, 1H, CH$^{hq\ 2}$) 6.35 (s, 2H, CH$^{mes}$), 6.28 (d j=7.2 Hz, CH$^{ind\ 1\ or\ 4}$), 5.48 (dd j=4.8 Hz, 1H, CH$^{hq\ 1}$), 3.89 (s, 4H, CH₂$^{mes}$), 2.36, 2.28, 2.08 (s, 18H, CH₃$^{mes}$).

$^{13}$C-NMR (δ, 20° C., CDCl₂, 300 MHz): Ru=C not observed, 204.3 (1C, C$_q$, Ru—C), 166.3 (C$_q$), 161.2 (C$_q$), 150.0 (CH), 145.8 (C$_q$), 145.1 (C$_q$), 143.1 (CH), 142.0 (C$_q$), 141.7 (CH), 140.4 (C$_q$), 137.9 (C$_q$), 137.5 (C$_q$), 137.3 (C$_q$), 136.8 (C$_q$), 136.4 (C$_q$), 136.3 (C$_q$), 136.4 (C$_q$), 136.3 (C$_q$), 136.2 (C$_q$), 133.3 (CH), 133.2 (CH), 130.0 (CH), 129.7 (CH), 129.6 (CH), 129.4 (CH), 129.3 (CH), 129.1 (CH), 128.5 (CH), 128.2 (CH), 128.1 (CH), 126.6 (CH), 126.0 (CH), 125.9 (C$_q$), 125.8 (CH), 125.4 (C$_q$), 120.9 (CH), 120.7 (CH), 120.1 (C$_q$), 118.5 (CH), 118.2 (C$_q$), 112.2 (C$_q$), 108.2 (C$_q$), 53.3 (2C, CH₂—N), 20.9, 20.3, 19.5 (18, CH₃).

Synthesis Way A

Equation 2

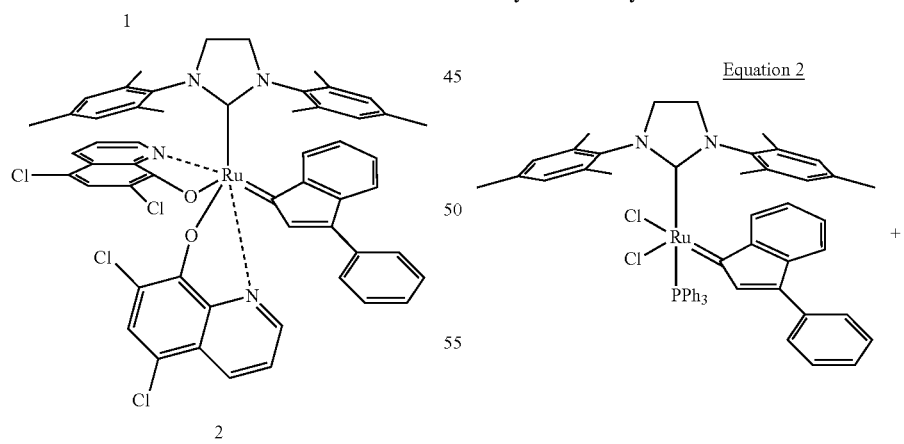

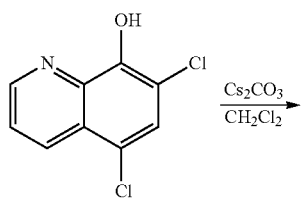

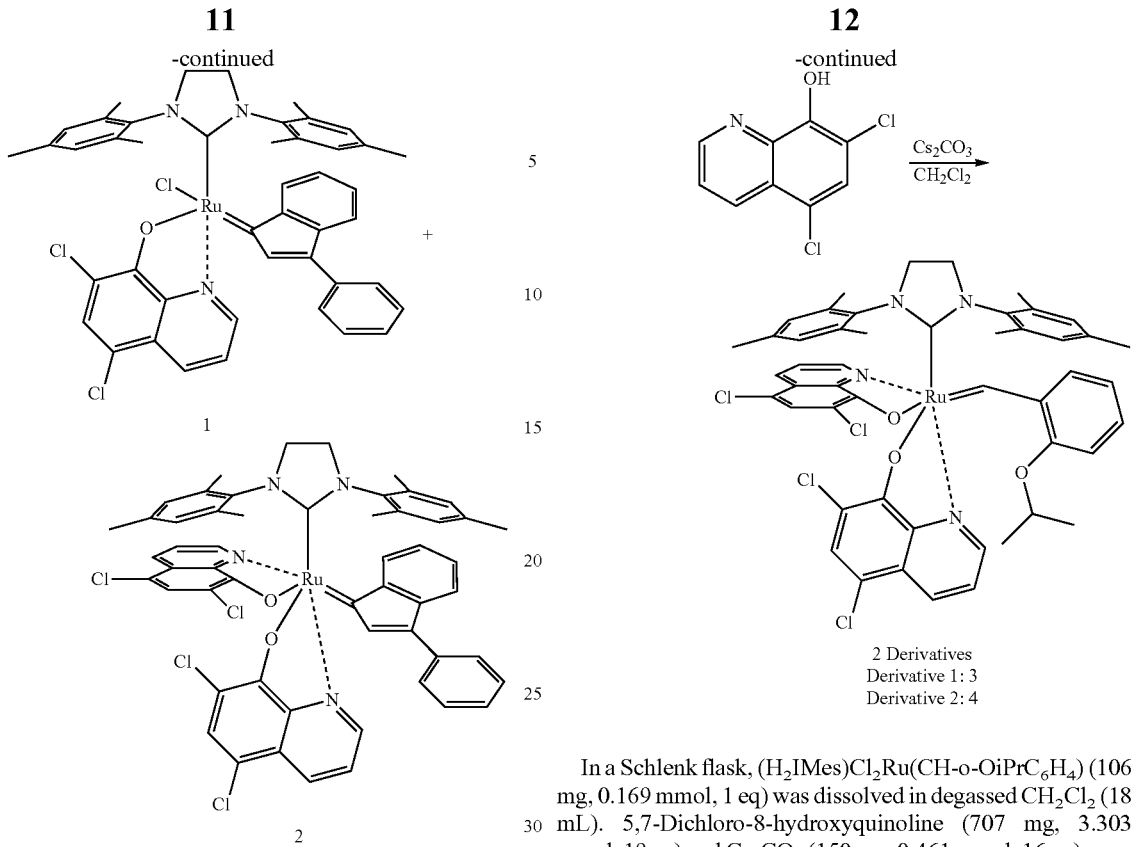

In a Schlenk flask (PPh$_3$)(H$_2$IMes)(Cl$_2$)Ru(3-phenyl-1H-inden-1-ylidene) (26 mg, 0.0278 mmol, 1 eq) was dissolved in degassed CH$_2$Cl$_2$ (≈3 mL). 5,7-Dichloro-8-hydroxyquinoline (88 mg, 0.411 mmol, 15 eq) and Cs$_2$CO$_3$ (150 mg, 0.461 mmol, 16 eq) were added. The reaction mixture was stirred in a Schlenk flask under argon atmosphere overnight.

The insoluble residue was filtered over celite. According to a TLC (CH/EE 5:1) two derivatives were formed. The two catalysts were separated via column chromatography (CH/EE 20:1) and fully characterized by NMR. Yield=73% (10.3 mg 1 and 8.4 mg 2).

Example 2

Preparation of (H$_2$IMes)(5,7-dichloro-8-quinolinolate)$_2$Ru(CH-o-OiPrC$_6$H$_4$)

Equation 3

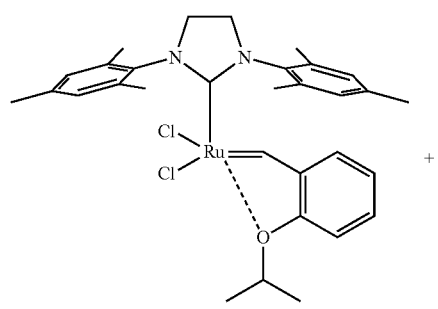

In a Schlenk flask, (H$_2$IMes)Cl$_2$Ru(CH-o-OiPrC$_6$H$_4$) (106 mg, 0.169 mmol, 1 eq) was dissolved in degassed CH$_2$Cl$_2$ (18 mL). 5,7-Dichloro-8-hydroxyquinoline (707 mg, 3.303 mmol, 19 eq) and Cs$_2$CO$_3$ (150 mg, 0.461 mmol, 16 eq) were added. The reaction mixture was stirred in a Schlenk flask under argon atmosphere overnight.

The insoluble residue was filtered over celite. According to a TLC (CH/EE 5:1) two derivatives were formed. The products were separated via column chromatography (CH/EE 5:1) and fully characterized by NMR and crystal structure analysis. Yield=83% (46.5 mg 3 and 91 mg 4).

3: $^1$H-NMR (δ, 20° C., CDCl$_3$, 300 MHz): 19.10 (s, 1H, Ru=CH), 8.09 (d J=4.04, 1H, CH$^{hq}$), 7.95 (d J=8.56; j=1.43, 1H, CH$^{hq}$), 7.68 (d J=8.43 j=1.30, 1H, CHP$^{hq}$), 7.49 (s, 1H, CH$^{hq}$), 7.17 (s, 1H, CH$^{hq}$), 7.05 (m, 2H, CH$^{hq}$), 6.56 (d J=8.04, 1H, CH$^{hq}$), 6.48 (s, 2H, CH$^{mes}$), 6.43 6,39 (?, 2H, CH$^{ph}$), 6.14 (s, 2H, CH$^{mes}$), 6.06 (2H, CH$^{hq+ph}$), 3.97 (5H, CH$_2$+CH$^{isoprop}$), 2.45 (s, 6H), 2.27 (s, 6H), 1.90 (s, 6H, CH$_3^{1, 1', 2, 2', 3, 3'}$), 1.43 (d, 3H, CH$_3^{isoprop}$), 1.05 (d, 3H, CH$_3^{isoprop}$).

3: $^{13}$C-NMR (δ, 20° C., CDCl$_3$, 75 MHz): 338.6 (1C, Ru=CH), 227.6 (1C, Ru—C), 162.6, 161.3, 149.7, 149.4, 149.0, 144.2, 143.2, 142.4, 142.3, 138.1 (C$_q$), 136.9 (C$_q$), 136.6 (C$_q$), 135.8 (C$_q$), 132.3 (CH), 131.7 (CH), 129.3 (CH), 129.2 (CH), 128.7, 127.7 (CH), 126.2, 125.8, 125.7, 122.2 (CH), 121.6 (CH), 121.0 (CH), 119.5 (CH), 118.9, 112.0, 109.2, 76.2 (1C, CH$^{isoprop}$), 51.6 (2C, CH$_2$—N), 23.1 (1C, CH$_3^{isoprop}$), 21.5 (1C, CH$_3^{isoprop}$), 20.8, 18.8, 18.5 (2C, CH$_3^{mes\ 7, 7', 8, 8', 9, 9'}$).

4: $^1$H-NMR (δ, 20° C., CDCl$_3$, 300 MHz): 18.23 (bs, 1H, Ru=CH), 9.00 (d j=4.67 Hz, 1H, CH$^{hq\ 1}$), 8.09 (d J=8.56 Hz, 1H, CH$^{hq\ 3}$), 7.83 (d J=8.30 Hz, 1H, CH$^{hq\ 3}$) 7.57 (s, 1H, CH$^{hq\ 4\ or\ 4}$), 7.12 (s, 1H, CH$^{hq\ 4\ or\ 4}$), 7.06 (q, 1H, CH$^{hq\ 2}$), 6.94 (t, 1h; CH$^{ph\ 3\ or\ 4}$), 6.59 (s, 2H, CH$^{mes\ 3+3'\ or\ 5+5'}$), 6.39 (d, 1H, CH$^{ph\ 2\ or\ 5}$), 6.26 (s, 2H, CH$^{mes\ 3+3'\ or\ 5+5'}$), (d, 1H, CH$^{ph\ 2\ or\ 5}$), (t, 1H, Ch$^{hq\ 2}$), 5.98 (t, 1H, CH$^{ph\ 3\ or\ 4}$), 5.32 (d j=4.54 Hz, 1H, CH$^{hq\ 1}$), 4.54 (m, 1H, CH$^{isoprop}$), 3.92 (q, 4H, CH$_2^{mes}$), 2.57 (s, 6H), 2.04 (s, 6H), 1.91 (s, 6H, CH$_3^{mes\ 7, 7', 8, 8', 9, 9'}$), 1.53 (d, 3H, CH$_3^{isoprop}$), 1.31 (d, 3H, CH$_3^{isoprop}$).

$^{13}$C-NMR (δ, 20° C., CDCl$_3$, 75 MHz): Ru=C not observed, 209.5 (1C, Ru—C), 166.4 (C$_q$), 160.9 (C$_q$), 147.7 (C$_q$), 146.7 (C$_q$), 147.1 (C$_q$), 146.7 (C$_q$), 164.5 (CH), 146.5 (CH), 144.9 (C$_q$), 141.2 (CH), 137.1 (C$_q$), 137.0 (C$_q$), 136.7 (C$_q$), 136.5 (C$_q$), 119.3 (C$_q$), 125.8 (C$_q$), 132.7 (CH), 132.2 (CH), 129.2 (CH), 129.1 (2C, CH), 129.0 (CH), 128.6 (CH), 127.9 (CH), 126.4 (C$_q$), 120.7 (CH), 120.1 (CH), 119.7 (CH), 118.0 (C$_q$), 111.3 (C$_q$), 110.5 (CH), 106.4 (C$_q$), 68.7 (1C, CH$^{isoprop}$) 51.7 (2C, CH$_2$), 22.7, 22.3 (2C, CH$_3^{isoprop}$), 20.9, 18.9, 18.1 (6C, CH$_3^{mes\ 7,\ 7',\ 8,\ 8',\ 9'}$).

Even if both of the catalysts possess two 5,7-dichloro-8-hydroxyquinolines, they show different NMR patterns. The different structures were revealed by X-ray diffraction. The crystals for the X-ray diffraction measurement were obtained by slow diffusion of Et$_2$O in a saturated solution of CH$_2$Cl$_2$. The two derivatives exhibit a different geometry considering the 8-quinolinolate substituents. In derivative 3, the oxygen atoms of the two quinolinolates are orientated trans to each other, while in derivative 4 these trans positions are occupied by an oxygen and a nitrogen atom of the two different quinolinolates.

Example 3

Preparation of (H$_2$IMes)Cl(5,7-dibromo-8-quinolinolate)Ru(3-phenyl-indenylidene) and (H$_2$IMes)(5,7-dibromo-8-quinolinolate)$_2$Ru (3-phenyl-indenylidene)

Equation 4:

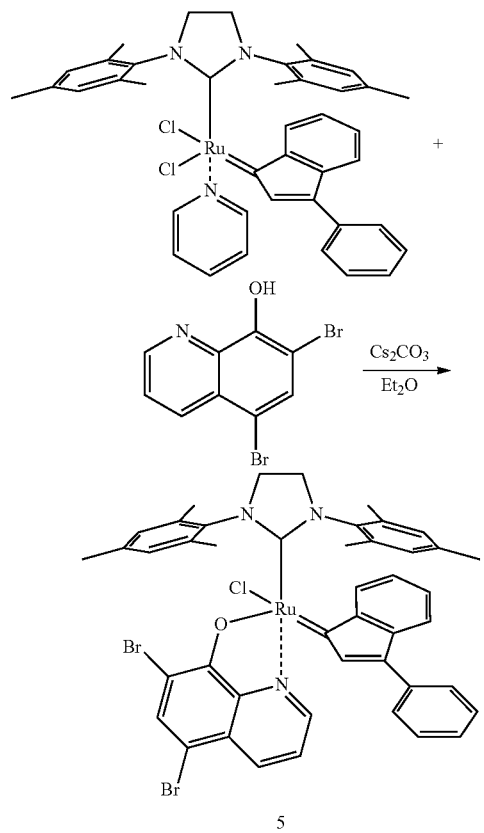

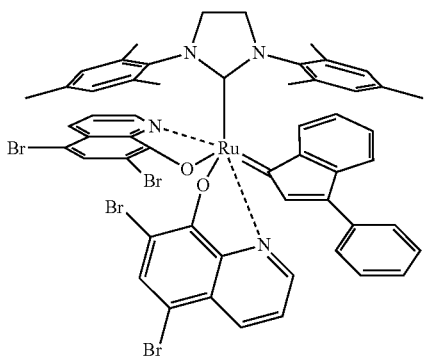

In a Schlenk flask, M31 (160 mg, 0.214 mmol, 1 eq) was dissolved in degassed Et$_2$O. 5,7-Dibromo-8-hydroxquinoline (960 mg, 3.169 mmol, 15 eq) and Cs$_2$CO$_3$ (1 g, 3.077 mmol, 14 eq) were added. The reaction mixture was stirred in a Schlenk flask under argon atmosphere for 12 hours. The reaction progress was followed by TLC (CH/EE 5:1). The insoluble residue was filtered over celite. According to a TLC (CH/EE 5:1) two products were formed. The new formed pre-catalysts were separated by column-chromatography (CH/EE 10:1), however, just the catalyst possessing one 8-quinolinolate was isolated.

5: $^1$H-NMR (δ, 20° C., CDCl$_3$, 300 MHz): 7.97 (d J=8.52, 1H, CH), 7.90 (d J=4.26, 1H, CH), 7.81 (s, 1H, CH$^{hq}$), 7.71 (d J=8.33, 1H, CH), 7.57 (s), 7.53 (bs, 3H, CH), 7.34 (bs, 3H, CH), 7.11 (d J=7.00, 1H, CH), 7.03 (q, 1H, CH), 6.49 (bs), 6.42 (s, 3H, CH+CH$^{mes}$), 6.27 (s, 2H, CH$^{mes}$), 6.18 (1H, bs, CH), 3.89 (s, 4H, CH$_2$), 2.30 (s, 6H, CH$_3$), 2.15 (bs, 6H, CH$_3$), 1.93 (s, 6H, CH$_3$).

$^{13}$C-NMR (δ, 20° C., CDCl$_3$, 300 MHz): Ru=C not observed, 241.9 (Ru—C), 168.8, 144.5, 144.1, 143.7, 143.0, 137.8, 137.0, 136.9, 136.6, 135.6, 135.2, 134.2, 133.4, 129.2, 129.1, 128.2, 127.8, 127.6, 127.5, 125.9, 122.6, 121.6, 117.4, 108.7, 108.3, 98.2, 3 C fehlen [???], 51.5 (2C, CH$_2^{mes}$), 21.0, 19.2 (18C, CH$_3^{mes}$).

Example 4

Preparation of (H$_2$IPr)(5,7-dichloro-8-quinolinolate)$_2$ Ru(3-phenyl-indenylidene)

Equation 5:

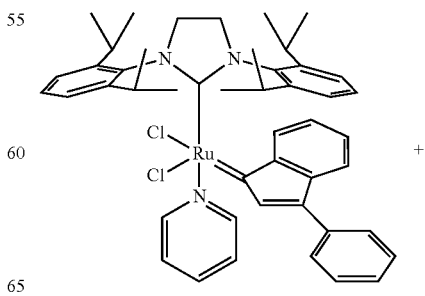

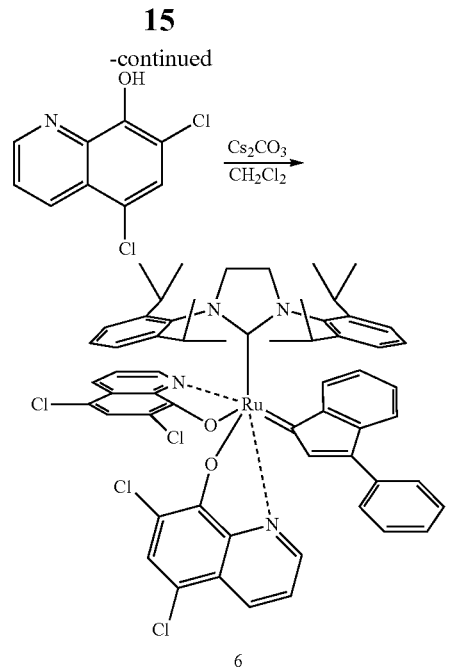

6

In a Schlenk flask, (Py)(H$_2$IPr)(Cl$_2$)Ru(3-phenyl-1H-inden-1-ylidene) (58 mg, 0.0697 mmol, 1 eq) was dissolved in degassed CH$_2$Cl$_2$ (≈6 mL). 5,7-Dichloro-8-hydroxyquinoline (136 mg; 0.6355 mmol; 9 eq) and Cs$_2$CO$_2$ (300 mg, 0.9230 mmol, 13 eq) were added. The reaction mixture was stirred in a Schlenk flask under argon atmosphere overnight. The insoluble residue was filtered over celite. According to a TLC (CH/EE 5:1) two products were formed. The products were separated via column chromatography (CH/EE 5:1). Derivative 1 was just formed in very low amount and not identified. Derivative 2 was identified by NMR spectroscopy ($^1$H, COSY, $^{13}$C and APT).

6: $^1$H-NMR (δ, 20° C., CDCl$_2$, 300 MHz): 8.03 (m, 3H, CH), 7.91 (s+d, 2H, CH), 7.67 (t, 1H, CH), 7.53 (t, 2H, CH), 7.41 (2s, 3H, CH), 7.30 (2s, 2H, CH), 7.21 (s, 1H, CH), 7.16 (m, 2H, CH), 6.79 (m, 2H, CH), 6.65 (m, 2H, CH), 6.47 (q, 1H, CH), 6.26 (m, 2H, CH), 5.9 (d, 1H J=4.51, CH$^{hq}$), 4.66, 4.17, 3.9, 3.76, 3.48 (8H, CH$^{isop}$+CH$_2$), 1.65, 1.34, 0.91, 0.61, 0.45 (s, 24H, CH$_3$9).

$^{13}$C-NMR (δ, 20° C., CDCl$_3$, 300 MHz): 286.2 (Ru=C), 206.6 (1C, Ru—C), 165.4 (1C, C$_q$), 162.0 (1C, C$_q$), 151.0 (1C, CH), 147.4, 146.4, 145.8, 145.6, 145.3, 145.2 (6C, C$_q$), 145.1 (1C, CH), 144.7 (1C, C$_q$), 144.0 (1C, CH), 141.2, 141.1, 139.3, 138.4, 137.0 (5C, C$_q$), 133.8, 132.6, 130.0, 129.8, 129.7, 128.9, 127.8, 127.7, 127.6, 126.0 (10C, CH), 125.8 (1C, C$_q$), 125.3 (1C, CH), 125.2 (1C, C$_q$), 124.8, 124.4, 124.3, 123.1, 121.5 (5C, CH), 120.4 (1C, C$_q$), 120.0, 117.9 (2C, CH), 117.7, 112.6, 108.4 (3C, C$_q$), 58.7, 55.9 (2C, CH$_2$), 29.7, 28.6, 28.5, 27.3, 26.9, 26.1, 25.6, 24.8, 24.6, 22.0, 21.9, 21.2 (12C, CH$^{isop}$+CH$_3$).

Example 5

In the following some polymerization features of the compounds of the present invention are presented.

As a benchmark polymerization reaction, the ROMP of endo/exo-norbornendimethylester was performed in solution, to gain information about the polymerization behaviour, as well as in a NMR tube, to study the kinetic performance of the catalysts Equation 6: Reaction equation of benchmark ROM polymerization of endo/exo-norbornendimethylester

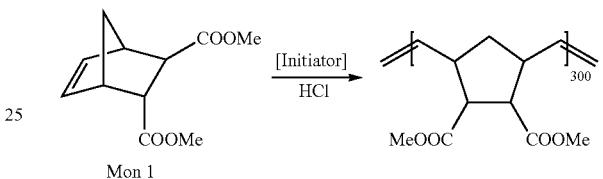

Defined solutions of pre-catalyst 1-6 and Mon 1 (300 eq, 0.01 mmol/mL) were prepared. The reactions were performed in CH$_2$Cl$_2$ for room temperature and in toluene for 80° C. polymerizations.

The first reactions were carried out without any activation agent added. No conversion was observed, even after 24 hours. Also attempts to activate the pre-catalysts by the means of heat or irradiation with UV-light failed. Therefore, the activation was accomplished using acid as the activation agent. HCl (50 eq etherical HCl relative to ruthenium or 2 drops of HCl in aqueous solution) was added to activate the reaction. The reaction was followed by TLC (CH:EE 3:1) and after complete conversion stopped with an excess of ethylvinylether. The Polymer was precipitated in vigorously stirred methanol, and the white to yellowish precipitate was sampled and dried in vacuum.

Molecular weights (Mn) and polydispersity indices (PDI) were determined using gel permeation chromatography (GPC) in THF against a polystyrene standard.

| Entry | Temp. [° C.] | Pre-catalyst | Activation | Time [h] | Conversion [%] | Isol. Yield [%] | Mn [kg/mol] | PDI |
|---|---|---|---|---|---|---|---|---|
| a | 20 | 1-6 | — | 24 | 0 | 0 | — | — |
| b | 80 | 1-6 | — | 24 | 0 | 0 | — | — |
| c | 20 | 1-6 | UV light | 24 | 0 | 0 | — | — |
| d | 20 | 1 | HCl eth. | 6.25 | 100 | 75 | 413 | 2.0 |
| e | 20 | 2 | HCl eth. | 2 | 100 | 78 | 181 | 1.9 |
| f | 20 | 3 | HCl eth. | 23 | 65 | 42 | 254 | 2.2 |
| g | 20 | 4 | HCl eth. | 4 | 100 | 85 | 148 | 2.4 |
| h | 20 | 5 | HCl eth. | 24 | 76 | 23 | 278 | 2.1 |
| i | 20 | 6 | HCl eth. | 2.15 | 100 | 45 | | |
| j | 20 | 1 | HCl wss. | | 95 | 72 | 392 | 2.0 |
| k | 20 | 2 | HCl wss. | 4.5 | 100 | | 205 | 2.0 |
| l | 20 | 3 | HCl wss. | 23 | 44 | 20 | 296 | 1.8 |
| m | 20 | 4 | HCl wss. | 4.5 | 100 | 78 | 266 | 1.8 |
| n | 20 | 5 | HCl wss. | 23 | 66 | 20 | 275 | 1.8 |
| o | 20 | 6 | HCl wss. | 2 | 100 | 58 | | |

-continued

| Entry | Temp. [°C.] | Pre-catalyst | Activation | Time [h] | Conversion [%] | Isol. Yield [%] | Mn [kg/mol] | PDI |
|---|---|---|---|---|---|---|---|---|
| p | 80 | 1 | HCl wss. | 2.25 | 100 | 84 | 411 | 2.1 |
| q | 80 | 2 | HCl wss. | 1 | 100 | 88 | 159 | 1.9 |
| r | 80 | 3 | HCl wss. | 24 | 77 | 46 | 132 | 2.3 |
| s | 80 | 4 | HCl wss. | 1 | 100 | 83 | 418 | 2.2 |
| t[a] | 80 | 4 | HCl wss. | 1 | 100 | 76 | 412 | 1.96 |
| U | 80 | 5 | HCl wss. | 1.25 | 100 | 81 | 466 | 2.3 |
| V | 80 | 6 | HCl wss. | 0.75 | 100 | | | |
| w[b] | 20 | 1 + 2 | HCl eth. | 3.5 | 100 | 77 | 173 | 1.9 |

[a]The pre-catalyst/monomer solution was kept at 80° C. for 24 hours, without any polymerization taking place and initiated after this 24 hours with HCl.
[b]Pre-catalysts 1 and 2 were used together, without separating them with column chromatography. Purification was just done by filtration of the insoluble residues.

Summarizing the results of the polymerization data it can be assumed, that the catalysts of the new invention exhibit a slow initiation and a faster propagation. The ratio $k_i/k_p$ is <1. Rising the reaction temperature decreases reaction times and in some cases increases conversion. Moreover, the results are not critically influenced whether etherical or aqueous HCl is used. The entries a and b and c represent the inactivity of the pre-catalysts without the addition of an activation agent. Entry t shows, that even after one day in solution at 80° C., pre-catalyst 4 remains stable and exhibits the same reactivity upon activation.

Additionally to polymerizations reactions using the pure initiators, tests with the unseparated mixture of pre-catalyst 1 and 2 were performed. The results are shown in entry w.

Figure 3:
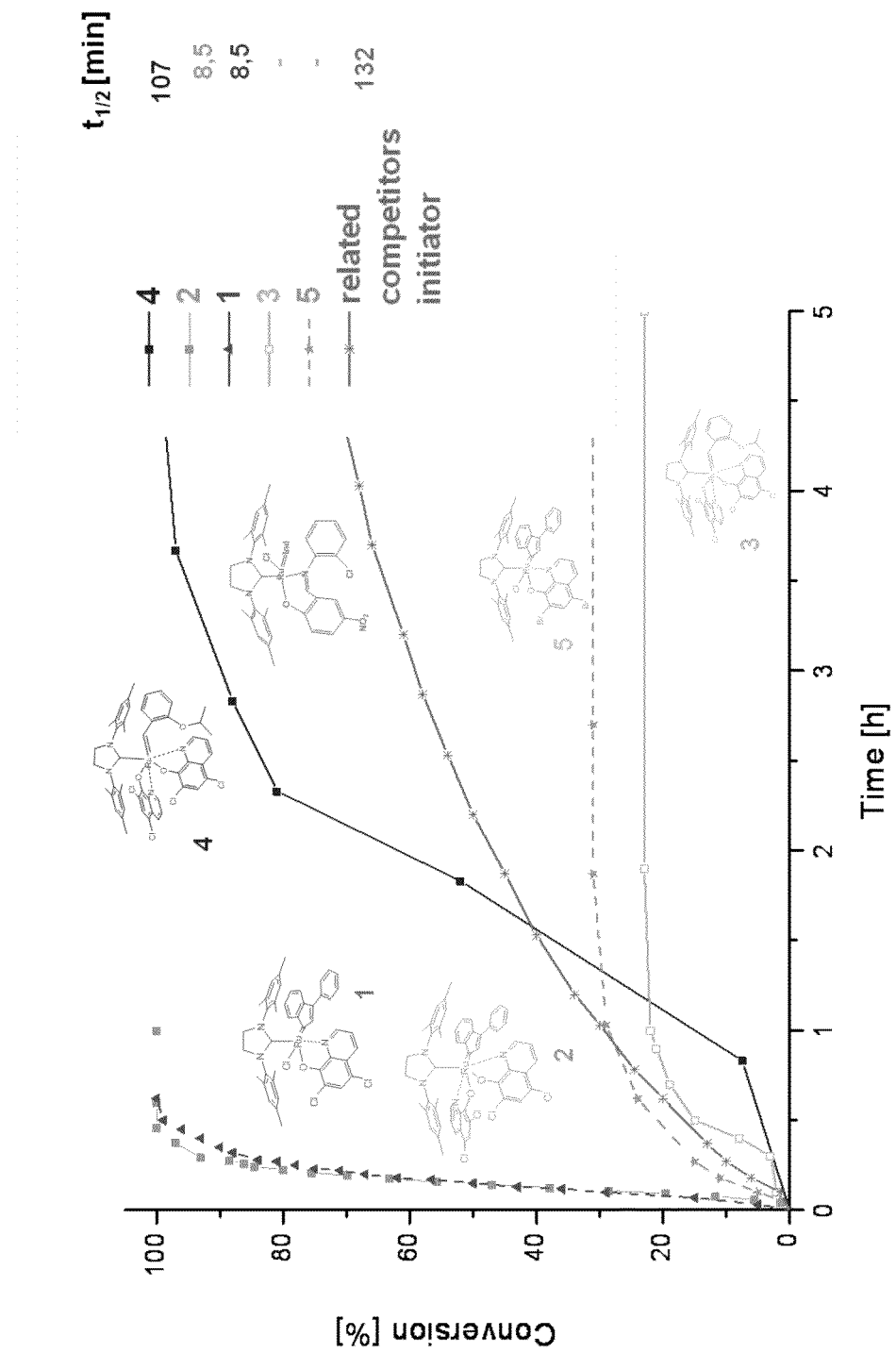
FIG. 3 shows kinetic plot of pre-catalyst 1-6 with the monomer endo/exo-norbornendimethylester (see example 5). The reaction conditions were [I]:[M] 1:50; 0.1 molar; $CDCl_3$, RT, 25 eq HCl eth. relative to [Ru]; reactions were performed under oxygen atmosphere.

As shown in FIG. 3 some derivatives, namely 1, 2 and 4, exhibit better polymerization characteristics under air, as related N—, O— chelating catalysts.

Example 6

In the following, some polymerization data regarding the solvent free polymerization of DCPD are presented. Due to the second double bond of DCPD, it tends to form a crosslinked polymer. These polymers exhibit good impact and chemical corrosion resistance.

Equation 2: Reaction equation of benchmark ROM polymerization of endo/exo-dicyclopentadiene.

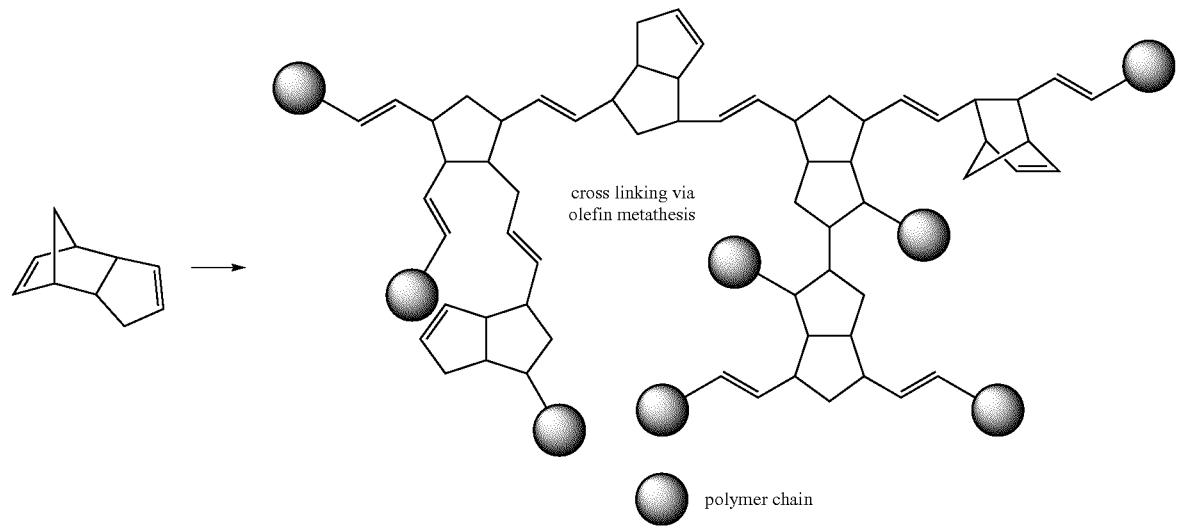

a) TGA-DTA Analysis

For the TGA-DTA measurements, a defined reaction solution of pre-catalysts (100 ppm) and DCPD were prepared. The corresponding amount of etherical HCl (25 eq relative to ruthenium) was added. To avoid polymerization before the measurements starts, the reaction solution was cooled with liquid nitrogen immediately after the HCl was added. A weighted portion of the frozen pre-catalyst/DCPC/HCl mixture was put promptly into the TGA/DSC (nitrogen flow rate of 50 mL/min) and measured with a temperature program of 3° C./min. The TGA is operated with a helium flow rate of 50 mL/min used in combination with a protective flow of 8 mL/min.

Figure 4:
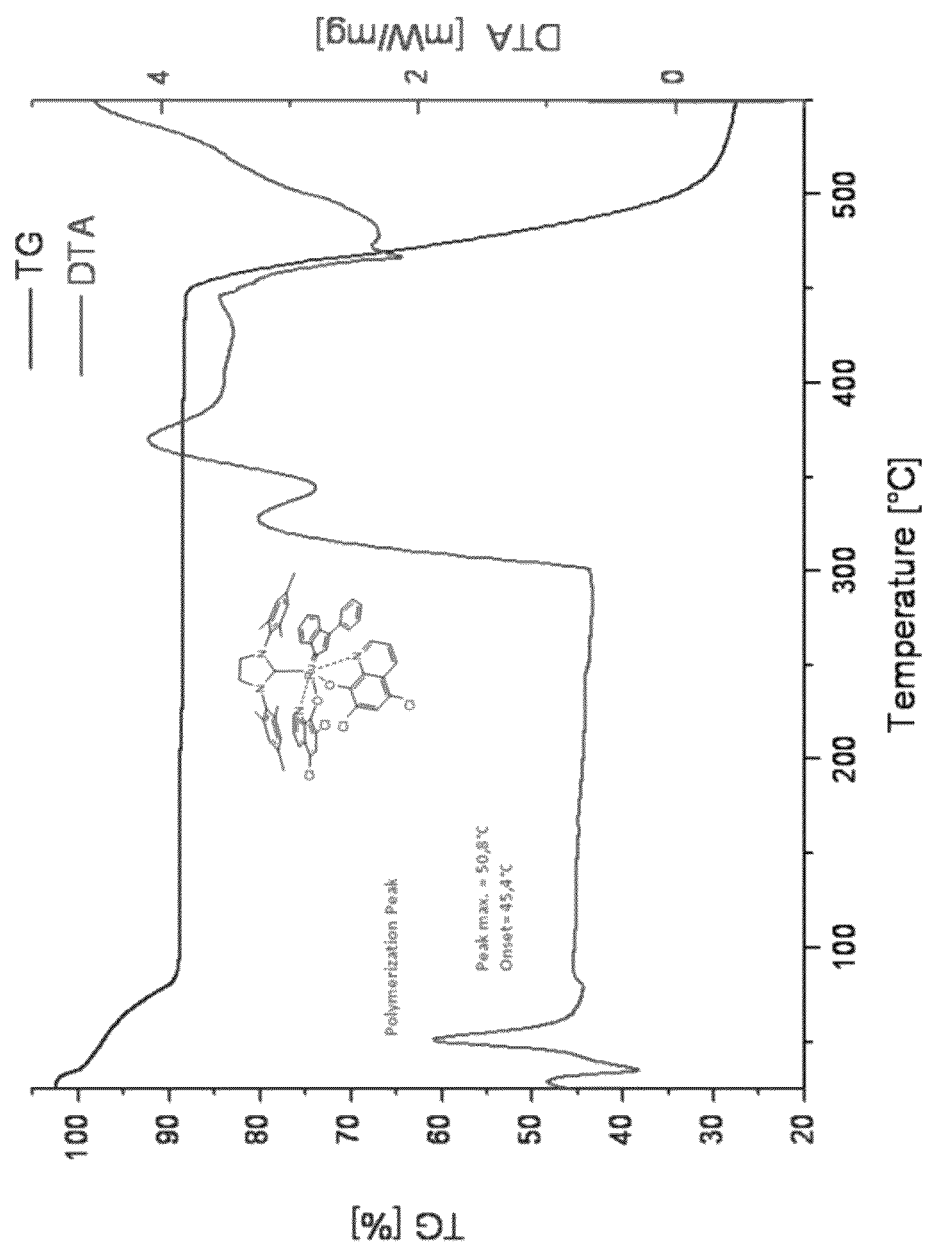
FIG. 4 shows a TGA-DTA measurement of DCPD with catalyst 2; ratio [I]:[DCPD]:[HCl] 1:10.000:50; temperature program: 3° C./min.

The TGA-DTA measurement gives insights into the polymerization behavior of the substance polymerization of DPCD. DCPD is prone to undergo a Retro-Diels-Alder reaction at higher temperatures, causing the mass loss during polymerization, under the measurement conditions. In FIG. 4 the substance polymerization of DCPD with catalyst 2 is shown.

b) Strain Measurement

To gain more information about the behavior of the new catalysts regarding the polymerization of DCPD, shoulder test bars were made and analyzed with a Shimadzu tensile stress test machine. To obtain the shoulder-test-bars, the appropriate amount of pre-catalyst was mixed with 28 mL of DCPD. The mixture was shacked, heated or if necessary put into an ultrasonic bath until the catalyst was totally dissolved. Afterwards, the corresponding amount of etherical HCl was added and the mixture put immediately into a cold shoulder-test-bar form. Until complete hardening of the test bar was observable, the form was kept in an at 60° C. temperate dry-box. Several shoulder test bars with varying [I]:[Mon] ratios were prepared.

Figure 5:
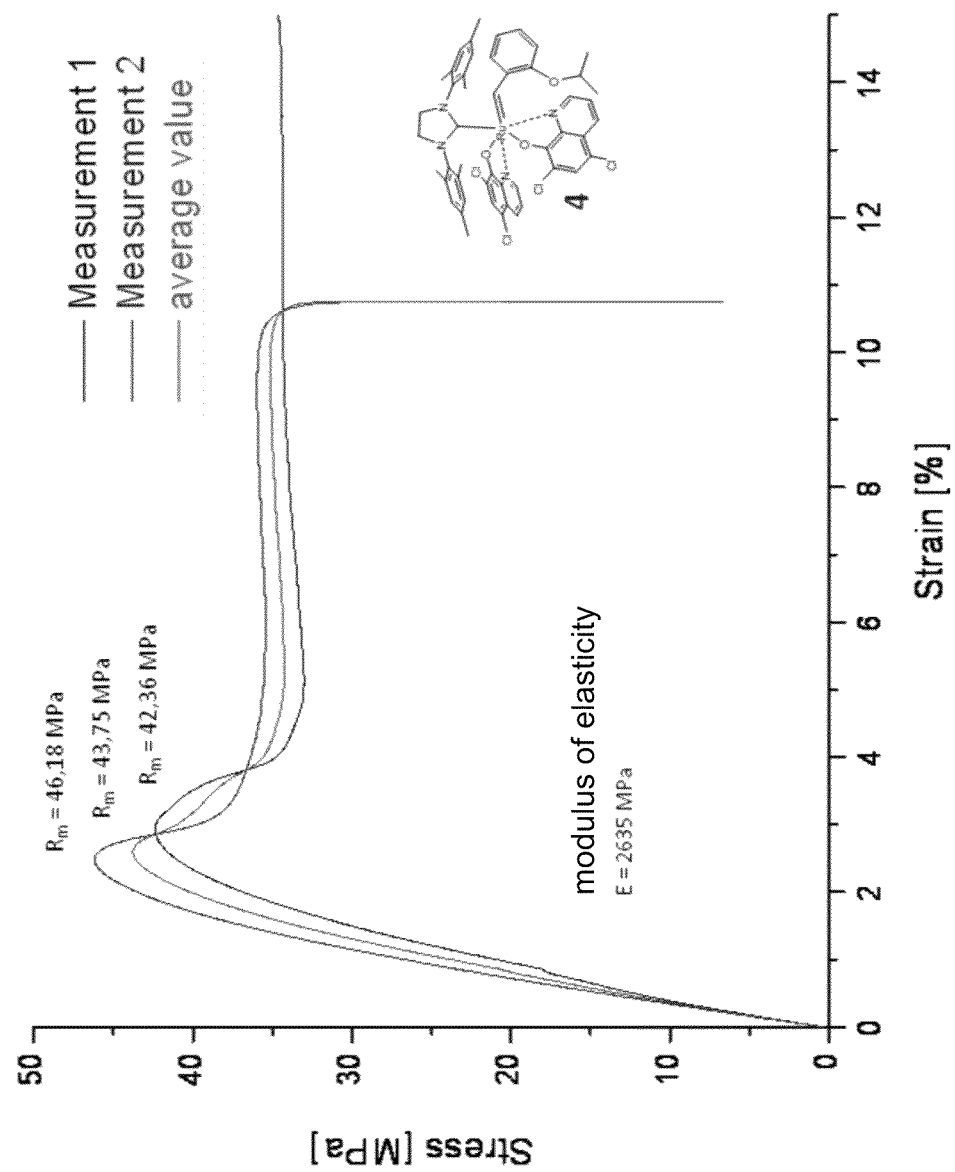
FIG. 5 shows a tensile test of DCPD shoulder test bar; [Ru]:[DCPD] 1:10.000; 50 eq HCl, 60° C.

The strain rate for the analysis was set with 1 mm/min. FIG. 5 shows an example of such a strain test. Ultimate strength values and the Young's modulus could be read out of the diagrams and compared with each other.

The maximum amount of pre-catalysts dissolved in DCPD for these experiments was 100 ppm.

The invention claimed is:

1. A compound having general formula (I)

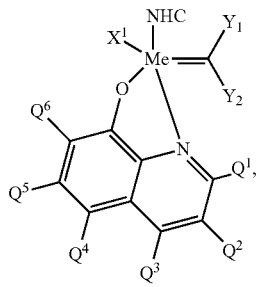

(I)

wherein $X^1$ is selected from the group consisting of halogens pseudohalogens, trifluoroacetate, carboxylates and a $\kappa^2$ (N,O) bound 8-quinolinolate of the general formula (II)

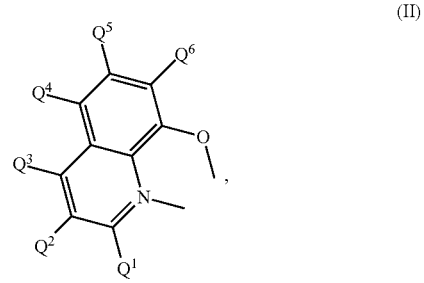

(II)

$Q^1, Q^2, Q^3, Q^4, Q^5$ and $Q^6$ are independently selected from the group consisting of hydrogen, halogens, cyano, $C_1$ to $C_6$-alkyl,aryl, benzyl, nitro,hydroxyl, sulfonic acid, arylsulfonyl, —$OR^a$, —$NR^a{}_2$, —$CX^b{}_3$, and —$COR^a$, wherein $R^a$ is H or $C_1$ to $C_6$-alkyl and $X^b$ is F, Cl or Br, $Y^1$ and $Y^2$ are independently selected from the group consisting of hydrogen $C_1$ to $C_6$-alkyl, aryl,

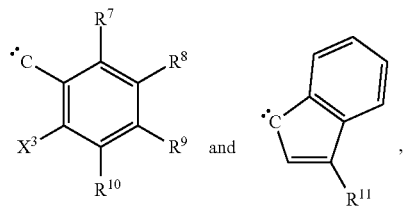

wherein $X^3$ is selected from the group consisting of hydrogen, —$OR^6$, —COH, —$COR^6$, —$COOR^6$ —$SR^6$, $SOR^6$, and $SO_2R^6$, wherein $R^6$ is optionally a functionalized, branched or unbranched $C_1$ to $C_6$-alkyl group $R^7$, $R^8$, $R^9$ and $R^{10}$ is independently selected from the group consisting of hydrogen, $C_1$ to $C_6$ alkyl, halogens, nitro and $C_1$ to $C_6$- alkoxy $R^{11}$ is a substituted or unsubstituted aryl group, NHC is a N-heterocyclic carbene and Me is a metal selected from the group consisting of ruthenium, molybdenum and tungsten.

2. The compound according to claim 1, wherein the N-heterocyclic carbene (NHC) is a saturated or unsaturated carbene of the general formula (III) or (IV)

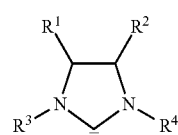

(III)

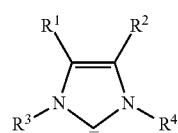

(IV)

wherein $R^1$ and $R^2$ are selected independently from the group consisting of hydrogen, halogen, $C_1$-$C_6$-alkyl and aryl or form a ring with 5 to 7 carbon atoms and $R^3$ and $R^4$ are selected independently from the group consisting of alkyl, aryl and phenyl, wherein the phenyl residue is optionally substituted three times with hydrogen, branched or unbranched $C_1$-$C_6$alkyl residues and/or halogen residues.

3. The compound according to claim 1, wherein the N-heterocyclic carbene (NHC) is selected from the group consisting of H$_2$IMes (1,3-dimesityl-imidazolidin-2-yliden), IMes (1,3-dimesityl-imidazol-2-yliden), SIPr (1,3-bis(2,6-diisopropylphenyl)-4,5-dihydroimidazol-2-yliden) and IPr (1,3-bis(2,6-diisopropylphenyl)-4,5-imidazol-2-yliden).

4. The compound according to claim 1, wherein Y$^1$ is selected from the group consisting of phenyl and phenylindenylidene and Y$^2$ is hydrogen.

5. The compound according to claim 1, wherein the 8-quinolinolate is selected from the group consisting of unsubstituted 8-quinolinolate, 5,7-dichloro-8-quinolinolate and 5,7-dibromo-8-quinolinolate quinolinolate.

6. The compound according to claim 1 wherein X$^1$ is Cl.

7. The compound according to claim 1, wherein X$^1$ is Cl, Br or I, and/or wherein R$^a$ is C$_1$ to C$_3$-alkyl, and/or wherein one or more of R$^7$, R$^8$, R$^9$ and R$^{10}$ are C$_1$ to C$_3$-alkyl, and/or wherein one or more of R$^7$, R$^8$, R$^9$ and/or R$^{10}$ is —OCH$_3$ and/or wherein adjacent two of R$^7$, R$^8$, R$^9$ and R$^{10}$ form an additional aromatic ring with each other.

8. The compound according to claim 1, wherein adjacent two of R$^7$, R$^8$, R$^9$ and R$^{10}$ form an additional aromatic ring with each other, which ring is selected from a substituted and an unsubstituted indenylidene ring.

9. A method of mixing a pre-catalyst for olefin metathesis and an olefin, comprising bringing the compound according to claim 1, as the pre-catalyst, into solution with or by the olefin.

10. The method according to claim 9, wherein the olefin metathesis is a ring opening metathesis polymerization of cyclic olefins, a metathesis of cyclic olefins, acyclic diene metathesis, a cross-metathesis of cyclic and acyclic olefins, a ring closing metathesis, a metathesis depolymerization of unsaturated polymers or a metathesis of functionalized olefins.

11. A compound having general formula (I)

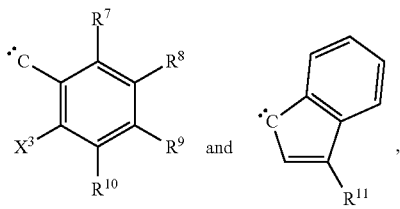

wherein X$^1$ is a κ$^2$ (N,O) bound 8-quinolinolate of the general formula (II)

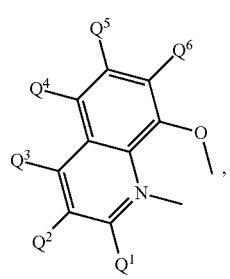

Q$^1$, Q$^2$, Q$^3$, Q$^4$, Q$^5$ and Q$^6$ are independently selected from the group consisting of hydrogen, halogens, cyano, C$_1$ to C$_6$-alkyl, aryl, benzyl, nitro, hydroxyl, sulfonic acid, arylsulfonyl, —OR$^a$, —NR$^a_2$, —CX$^b_3$, and —COR$^a$, wherein R$^a$ is H or C$_1$ to C$_6$-alkyl and X$^b$ is F, Cl or Br, Y$^1$ and Y$^2$ are independently selected from the group consisting of hydrogen C$_1$ to C$_6$-alkyl, aryl,

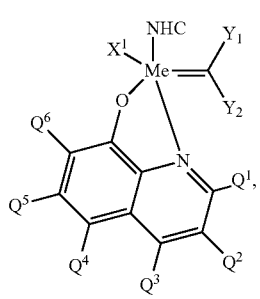

wherein

X$^3$ is selected from the group consisting of hydrogen, —OR$^6$, —COH, —COR$^6$, —COOR$^6$ —SR$^6$, SOR$^6$, and SO$_2$R$^6$, wherein R$^6$ is optionally a functionalized, branched or unbranched C$_1$ to C$_6$-alkylgroup R$^7$, R$^8$, R$^9$ and R$^{10}$ are independently selected from the group consisting of hydrogen, C$_1$ to C$_6$ alkyl, halogen, nitro and C$_1$ to C$_6$- alkoxy, R$^{11}$ is a substituted or unsubstituted aryl group, NHC is a N-heterocyclic carbene and Me is a metal selected from the group consisting of ruthenium, molybdenum and tungsten.

12. The compound according to claim 11, wherein the N-heterocyclic carbene (NHC) is a saturated or unsaturated carbene of the general formula (III) or (IV)

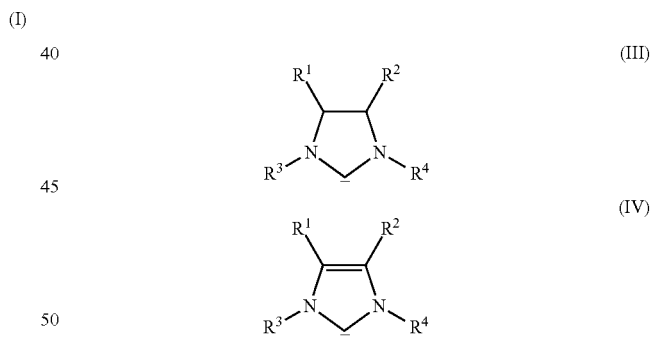

wherein R$^1$ and R$^2$ are selected independently from the group consisting of hydrogen, halogen, C$_1$-C$_6$-alkyl and aryl or form a ring with 5 to 7 carbon atoms and R$^3$ and R$^4$ are selected independently from the group consisting of alkyl, aryl and phenyl, wherein the phenyl residue is optionally substituted three times with hydrogen, branched or unbranched C$_1$-C$_6$ alkyl residues and/or halogen residues.

13. The compound according to claim 11, wherein the N-heterocyclic carbene (NHC) is selected from the group consisting of H$_2$IMes(1,3-dimesityl-imidazolidin-2-yliden), IMes (1,3-dimesityl-imidazol-2-yliden), SIPr (1,3-bis(2,6-diisopropylphenyl)-4,5-dihydroimidazol-2-yliden) and IPr (1,3-bis(2,6-diisopropylphenyl)-4,5-imidazol-2-yliden).

14. The compound according to claim 11, wherein $Y^1$ is selected from the group consisting of phenyl and phenyl-indenylidene and $Y^2$ is hydrogen.

15. The compound according to claim 11, wherein the 8-quinolinolate is selected from the group consisting of unsubstituted 8-quinolinolate, 5,7-dichloro 8-quinolinolate and 5,7-dibromo 8-quinolinolate.

16. The compound according to claim 11, wherein $X^1$ is Cl.

17. The compound according to claim 11, wherein $R^a$ is $C_1$ to $C_3$-alkyl and/or wherein one or more of $R^7$, $R^8$, $R^9$ and $R^{10}$ is —$OCH_3$.

18. A method of mixing a pre-catalyst for olefin metathesis and an olefin, comprising bringing the compound according to claim 11, as the pre-catalyst, into solution with or by the olefin.

19. The method according to claim 18, wherein the olefin metathesis is a ring opening metathesis polymerization of cyclic olefins, a metathesis of cyclic olefins, acyclic diene metathesis, a cross-metathesis of cyclic and acyclic olefins, a ring closing metathesis, a metathesis depolymerization of unsaturated polymers or a metathesis of functionalized olefins.

20. A method for olefin metathesis, in the presence of a compound comprising a step of bringing into contact at least one olefin with a compound, wherein the olefin metathesis is initiated via the addition of acid, wherein the compound has the general formula (I)

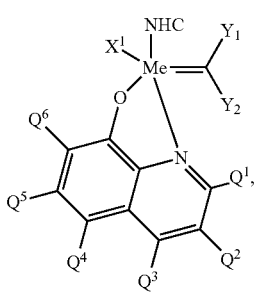
(I)

wherein $X^1$ is selected from the group consisting of halogens, pseudohalogens, trifluoroacetate, carboxylates and a $\kappa^2$ (N,O) bound 8-quinolinolate of the general formula (II)

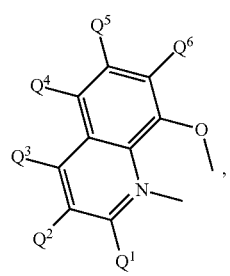
(II)

$Q^1, Q^2, Q^3, Q^4, Q^5$ and $Q^6$ are independently selected from the group consisting of hydrogen, halogens, cyano, $C_1$ to $C_6$-alkyl, aryl, benzyl, nitro, hydroxyl, sulfonic acid, arylsulfonyl, —$OR^a$, —$NR^a_2$, —$CX^b_3$, —$COR^a$, wherein $R^a$ is H or $C_1$ to $C_6$-alkyl and $X^b$ is F, Cl or Br, $Y^1$ and $Y^2$ are independently selected from the group consisting of hydrogen $C_1$ to $C_6$-alkyl, aryl,

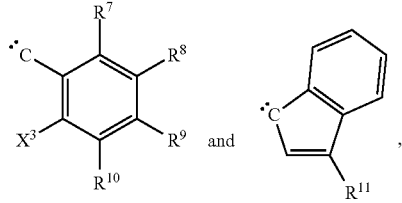

wherein
$X^3$ is selected from the group consisting of hydrogen, —$OR^6$, —COH, —$COR^6$, —$COOR^6$ —$SR^6$, $SOR^6$, and $SO_2R^6$, wherein $R^6$ is optionally a functionalized, branched or unbranched $C_1$ to $C_6$-alkyl group $R^7$, $R^8$, $R^9$ and $R^{10}$ is independently selected from the group consisting of hydrogen, $C_1$ to $C_6$ alkyl, halogens, nitro and $C_1$ to $C_6$- alkoxy, $R^{11}$ is a substituted or unsubstituted aryl group, NHC is a N-heterocyclic carbene and Me is a metal selected from the group consisting of ruthenium, molybdenum and tungsten.

21. The method according to claim 20, wherein the method is for ring opening metathesis polymerization of cyclic olefins.

22. The method according to claim 20, wherein the olefin metathesis is the ring opening metathesis polymerization of dicyclopentadiene.

23. The method according to claim 20, wherein $X^1$ is Cl, Br or I, and/or wherein $R^a$ is $C_1$ to $C_3$-alkyl, and/or wherein one or more of $R^7$, $R^8$, $R^9$ and $R^{10}$ are $C_1$ to $C_3$-alkyl, and/or wherein one or more of $R^7$, $R^8$, $R^9$ and/or $R^{10}$ is —$OCH_3$ and/or wherein adjacent two of $R^7$, $R^8$, $R^9$ and $R^{10}$ form an additional aromatic ring with each other.

24. The method according to claim 20, wherein adjacent two of $R^7$, $R^8$, $R^9$ and $R^{10}$ form an additional aromatic ring with each other, which ring is selected from a substituted and an unsubstituted indenylidene ring.

25. A method for olefin metathesis, in the presence of a compound comprising a step of
bringing into contact at least one olefin with a compound, wherein the olefin metathesis is initiated via the addition of acid, wherein the compound has the general formula (I)

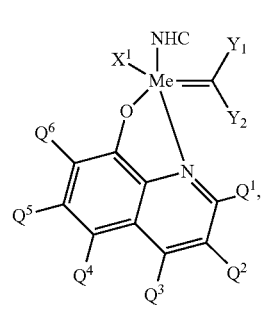
(I)

wherein $X^1$ is a $\kappa^2$ (N,O) bound 8-quinolinolate of the general formula (II)

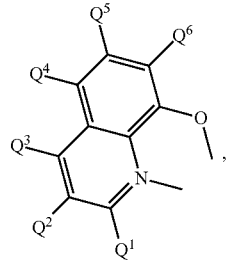

(II)

$Q^1, Q^2, Q^3, Q^4, Q^5$ and $Q^6$ are independently selected from the group consisting of hydrogen, halogens, cyano, $C_1$ to $C_6$-alkyl, aryl, benzyl, nitro, hydroxyl, sulfonic acid, arylsulfonyl, —$OR^a$, —$NR^a_2$, —$CX^b_3$, —$COR^a$, wherein $R^a$ is H or $C_1$ to $C_6$-alkyl and $X^b$ is F, Cl or Br, $Y^1$ and $Y^2$ are independently selected from the group consisting of hydrogen $C_1$ to $C_6$-alkyl, aryl,

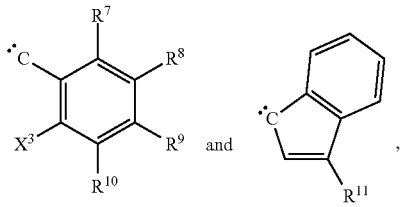

wherein $X^3$ is selected from the group consisting of hydrogen, —$OR^6$, —COH, —$COR^6$, —$COOR^6$ —$SR^6$, $SOR^6$, and $SO_2R^6$, wherein $R^6$ is optionally a functionalized, branched or unbranched $C_1$ to $C_6$-alkylgroup $R^7$, $R^8$, $R^9$ and $R^{10}$ are independently selected from the group consisting of hydrogen, $C_1$ to $C_6$ alkyl, halogen, nitro and $C_1$ to $C_6$- alkoxy, $R^{11}$ is a substituted or unsubstituted aryl group, NHC is a N-heterocyclic carbene and Me is a metal selected from the group consisting of ruthenium, molybdenum and tungsten.

26. The method according to claim 25, wherein the method is for ring opening metathesis polymerization of cyclic olefins.

27. The method according to claim 25, wherein the olefin metathesis is the ring opening metathesis polymerization of dicyclopentadiene.

28. The method according to claim 25, wherein $R^a$ is C1 to C3-alkyl, and/or wherein one or more of $R^7$, $R^8$, $R^9$ and $R^{10}$ is —$OCH_3$, and/or wherein adjacent two of $R^7$, $R^8$, $R^9$ and $R^{10}$ form an additional aromatic ring with each other.

* * * * *